United States Patent
Gregorich (10) Patent No.: US 7,235,093 B2
(45) Date of Patent: Jun. 26, 2007

(54) MECHANISM TO IMPROVE STENT SECUREMENT

(75) Inventor: Daniel Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 157 days.

(21) Appl. No.: 10/441,666

(22) Filed: May 20, 2003

(65) Prior Publication Data

US 2004/0236406 A1   Nov. 25, 2004

(51) Int. Cl.
*A61F 2/06* (2006.01)
(52) U.S. Cl. .................................................. 623/1.11
(58) Field of Classification Search ............... 623/1.11, 623/1.18, 1.23
See application file for complete search history.

(56) References Cited

U.S. PATENT DOCUMENTS

| | | | |
|---|---|---|---|
| 4,655,771 A | 4/1987 | Wallsten | 623/1 |
| 4,735,665 A | 4/1988 | Miyauchi et al. | 156/69 |
| 4,740,207 A | 4/1988 | Kreamer | 623/1 |
| 4,950,227 A | 8/1990 | Savin et al. | 604/8 |
| 4,954,126 A | 9/1990 | Wallsten | 600/36 |
| 5,061,275 A | 10/1991 | Wallsten et al. | 623/1 |
| 5,108,416 A | 4/1992 | Ryan et al. | 606/194 |
| 5,116,318 A | 5/1992 | Hillstead | 604/96 |
| 5,226,880 A | 7/1993 | Martin | 604/99 |
| 5,387,235 A * | 2/1995 | Chuter | 623/1.11 |
| 5,409,495 A | 4/1995 | Osborn | 606/108 |
| 5,445,646 A | 8/1995 | Euteneuer et al. | 606/198 |
| 5,476,476 A | 12/1995 | Hillstead | 606/194 |
| 5,556,414 A * | 9/1996 | Turi | 623/1.11 |
| 5,591,197 A * | 1/1997 | Orth et al. | 623/1.16 |
| 5,607,442 A * | 3/1997 | Fischell et al. | 623/1.18 |
| 5,741,327 A * | 4/1998 | Frantzen | 623/1.34 |
| 5,944,726 A | 8/1999 | Blaeser et al. | 606/108 |
| 5,968,096 A | 10/1999 | Whitson et al. | 623/15 |
| 5,972,018 A | 10/1999 | Israel et al. | 606/198 |
| 5,976,155 A | 11/1999 | Foreman et al. | 606/108 |
| 6,007,543 A | 12/1999 | Ellis et al. | 606/108 |
| 6,068,634 A | 5/2000 | Lorentzen Cornelius et al. | 606/108 |
| 6,077,273 A | 6/2000 | Euteneuer et al. | 606/108 |
| 6,110,180 A | 8/2000 | Foreman et al. | 606/108 |
| 6,123,712 A | 9/2000 | Di Caprio et al. | 606/108 |
| 6,132,461 A | 10/2000 | Thompson | 623/1.15 |
| 6,159,227 A | 12/2000 | Di Caprio et al. | 606/192 |
| 6,179,817 B1 * | 1/2001 | Zhong | 604/265 |
| 6,183,505 B1 | 2/2001 | Mohn, Jr. et al. | 623/1.11 |
| 6,258,099 B1 | 7/2001 | Mareiro et al. | 606/108 |
| 6,264,683 B1 | 7/2001 | Stack et al. | 623/1.11 |

(Continued)

FOREIGN PATENT DOCUMENTS

EP    0 442 657 A2    8/1991

(Continued)

*Primary Examiner*—Corrine McDermott
*Assistant Examiner*—Christopher Prone
(74) *Attorney, Agent, or Firm*—Vidas, Arrett & Steinkraus, P.A.

(57) ABSTRACT

The present invention comprises a securement member to improve securement of a stent upon an expandable balloon and delivery catheter, and to constrain portions of the stent before and during stent deployment. Generally, the securement member comprises a securement connector arranged to engage a catheter, at least one flexible connecting member coupled to the securement connector, and a locking member arranged to engage a portion of a stent.

21 Claims, 7 Drawing Sheets

U.S. PATENT DOCUMENTS

| | | |
|---|---|---|
| 6,287,331 B1 * | 9/2001 | Heath .................... 623/1.15 |
| 6,309,402 B1 | 10/2001 | Jendersee et al. ........... 606/198 |
| 6,350,277 B1 | 2/2002 | Kocur .................... 623/1.11 |
| 6,387,118 B1 | 5/2002 | Hanson .................... 623/1.11 |
| 6,468,299 B2 | 10/2002 | Stack et al. ............... 623/1.11 |
| 6,478,814 B2 | 11/2002 | Wang et al. ............... 623/1.12 |
| 6,494,906 B1 | 12/2002 | Owens .................... 623/1.11 |
| 6,506,201 B2 | 1/2003 | Di Caprio et al. ........... 606/192 |
| 6,554,841 B1 | 4/2003 | Yang .................... 606/108 |
| 6,558,415 B2 | 5/2003 | Thompson ................. 623/1.16 |
| 6,569,192 B1 | 5/2003 | Foreman et al. ............ 623/1.11 |
| 6,589,251 B2 | 7/2003 | Yee et al. .................... 606/108 |
| 6,673,107 B1 * | 1/2004 | Brandt et al. ............... 623/1.35 |
| 6,797,001 B2 * | 9/2004 | Mathis et al. ............... 623/2.37 |
| 6,818,013 B2 * | 11/2004 | Mitelberg et al. ........... 623/1.15 |
| 6,837,901 B2 * | 1/2005 | Rabkin et al. ............. 623/1.11 |
| 2002/0055767 A1 | 5/2002 | Forde et al. ................ 623/1.11 |
| 2002/0120322 A1 | 8/2002 | Thompson et al. ........ 623/1.11 |
| 2002/0156519 A1 | 10/2002 | Di Caprio et al. ......... 623/1.11 |
| 2003/0033000 A1 | 2/2003 | Di Caprio et al. .......... 623/1.11 |
| 2003/0074043 A1 | 4/2003 | Thompson ................. 623/1.11 |
| 2003/0074044 A1 | 4/2003 | Randby et al. ............. 623/1.11 |

FOREIGN PATENT DOCUMENTS

| | | |
|---|---|---|
| EP | 0442657 A2 * | 8/1991 |
| EP | 1 157 673 A2 | 11/2001 |
| WO | WO98/07388 | 2/1998 |
| WO | WO02/067782 A3 | 5/2003 |

* cited by examiner

MECHANISM TO IMPROVE STENT SECUREMENT

BACKGROUND OF THE INVENTION

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter, and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Inflation expandable stents are crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents.

There is currently a drive in the market to reduce the wall thickness of expandable coronary stents. Clinical results have shown that a reduced stent wall thickness improves vascular response.

There is also a market drive to make stents more flexible, allowing physicians to more easily maneuver stents through the bodily lumen, especially through the tortuous paths common in small vessels.

Thus, present stents commonly combine a thin wall thickness with high flexibility, which leads to various drawbacks associated with stent delivery. Stents with a reduced wall thickness typically have reduced strength in all directions. A stent with reduced strength has less ability to remain secure on the balloon and delivery catheter in the reduced state. Therefore, the stent has an increased risk of shifting positions on the catheter as it is maneuvered through the body. The stent must be able to securely maintain its axial position on the delivery catheter without translocation of its proximal or distal ends.

Reducing stent wall thickness may also reduce the axial strength of the stent. Lowered axial rigidity allows the stent to more easily pass through curved bodily vessels but can also lead to difficulty in stent placement during expansion.

When a stent with low axial rigidity is expanded by a balloon catheter, the stent may experience increased shortening or lengthening. If balloon inflation begins at the ends and continues inward, the deployed stent often has a shorter overall length after expansion. Conversely, if balloon inflation begins at the center and moves outwardly, the stent often experiences lengthening upon deployment.

Inflation expandable stent delivery and deployment assemblies are known which utilize restraining means that overlie the stent during delivery. U.S. Pat. No. 4,950,227 to Savin et al discusses an expandable stent delivery system in which a sleeve overlaps the distal or proximal margin (or both) of the stent during delivery. During expansion of the stent at the deployment site, the stent margins are freed of the protective sleeve(s). U.S. Pat. No. 5,403,341 to Solar relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al. describes a stent introducer system which uses one or two flexible end caps and an annular socket surrounding the balloon to position the stent during introduction to the deployment site.

These known methods typically release the stent early in the balloon inflation procedure and do not maintain the axial dimensions of the stent during inflation.

There remains a need for stent delivery systems that constrain the axial dimensions of the stent until the stent is fully expanded.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, the present invention is directed to a device for preventing stent movement during delivery. The device includes a securement connector arranged to engage a catheter, at least one flexible connecting member and at least one locking member arranged to engage a portion of a stent. The device is capable of constraining portions of the stent throughout expansion of the stent.

In another embodiment, the present invention is directed to a stent delivery system including a catheter, an expandable balloon a radially expandable stent and at least one radially expandable constrainment member. The constrainment member has a first end coupled to said catheter and a second end having at least one portion arranged to engage the stent. The constrainment member may remain engaged with the stent throughout expansion of the balloon.

In another embodiment, the present invention is directed to a stent delivery system including a catheter, an expandable balloon a radially expandable stent and at least one radially expandable constrainment member. The constrainment member generally comprises a circumferential band having a plurality of openings therethrough and at least one engaging portion. The constrainment member is arranged to at least partially overlay the balloon, and the at least on engaging portion is arranged to engage the stent. When the constrainment member and the stent are engaged, movement of the stent in the axial direction is prevented.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the present invention is directed to a stent securement member 10 as depicted in FIGS. 1-4. The securement member 10 generally comprises a securement connector 14, a flexible connecting member 18 and a locking or engaging member 22.

The securement member 10 may be used with a stent 28 having an engagable portion 30 desirably located at the one or both ends of the stent 28. The locking member 22 is arranged to engage the stent engagable portion 30 and thereby constrain movement of the stent 28. Desirably, movement of the stent 28 at the stent engagable portion 30 will be constrained in two dimensions. The securement member 10 will prevent movement in the stent axial direction, as well as preventing rotation of the stent 28 about the balloon. Desirably, the securement member 10 will not restrain movement in the direction of radial expansion of the stent 28.

Figure 1:
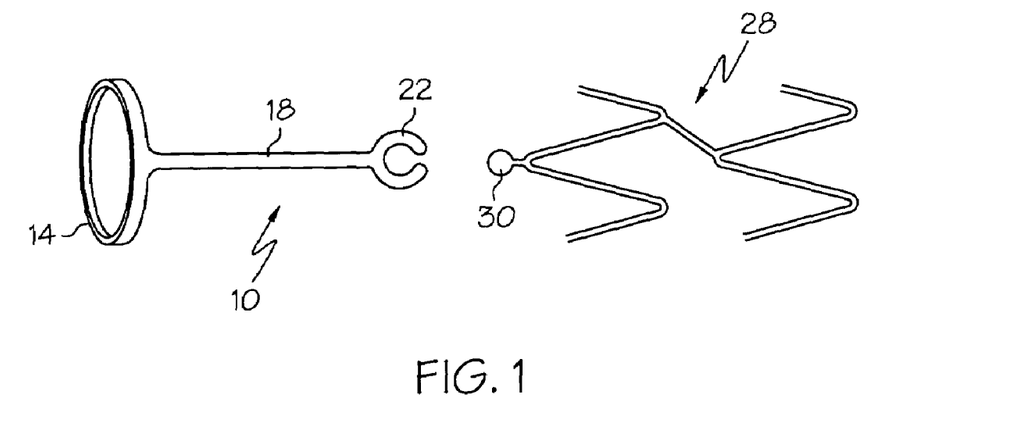
FIG. 1 is a perspective view of an embodiment of an inventive stent securement member.
Figure 2:
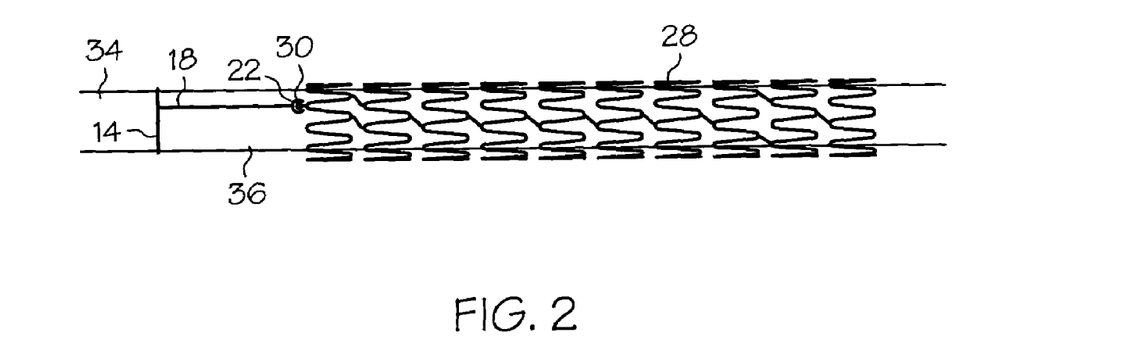
FIG. 2 is a perspective view of an embodiment of an inventive stent securement member placed on a catheter with a stent in the reduced state.

The securement member 10 will typically be used during stent delivery in conjunction with a catheter 34 and an expansion balloon 36. A balloon expandable stent 28 is typically crimped in a reduced state around a balloon 36 and catheter 34. The securement member 10 may be placed upon the catheter 34 with the locking member 22 engaging the stent engagable portion 30. The securement connector 14 may be coupled to the catheter 34 shaft, desirably by thermal bonding, adhesive bonding, swaging or by having a diameter of appropriate size to frictionally engage the catheter 34. Although the securement connector 14 desirably encircles the catheter 34, the securement connector 14 may be of any size, shape or material that adequately engages the catheter 34. The flexible connecting member 18 desirably overlays a portion of the expandable balloon 36 when the securement member 10 is in place.

The flexible connecting member 18 is desirably made from a shape memory material. The shape memory material may be a metal such as NiTi, CuZnAl, CuAlNi, MP35N, Elgiloy, Phynox, TiPtNi, TiPdNi, Cu—Zn, Cu—Al, Fe—Cr—Ni, Fe—Pd or Fe—Pt. The shape memory material may also be a polymer such as polymethylmethacrylate, polyvinylchloride, polynorbornene, trans-polyisoprene, polyurethane, styrene-butadiene copolymer or polyethylene. Further, the flexible connecting member 18 desirably will normally return to this reduced configuration.

Figure 3:
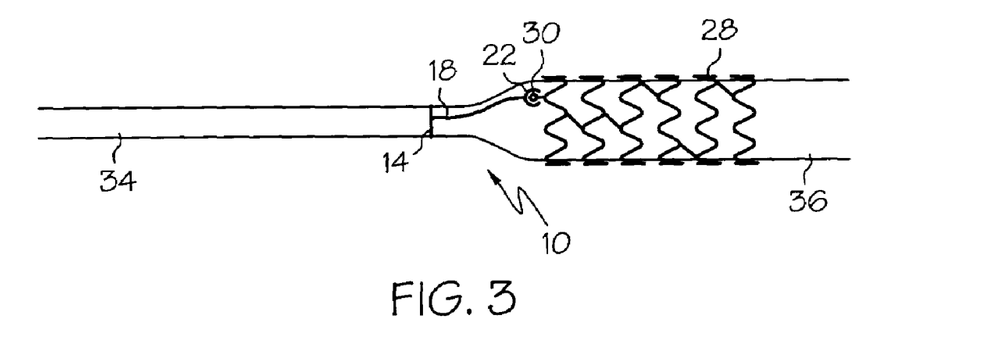
FIG. 3 is a perspective view of an embodiment of an inventive stent securement member placed on a catheter with a stent, wherein the expansion balloon is expanded.
Figure 4:
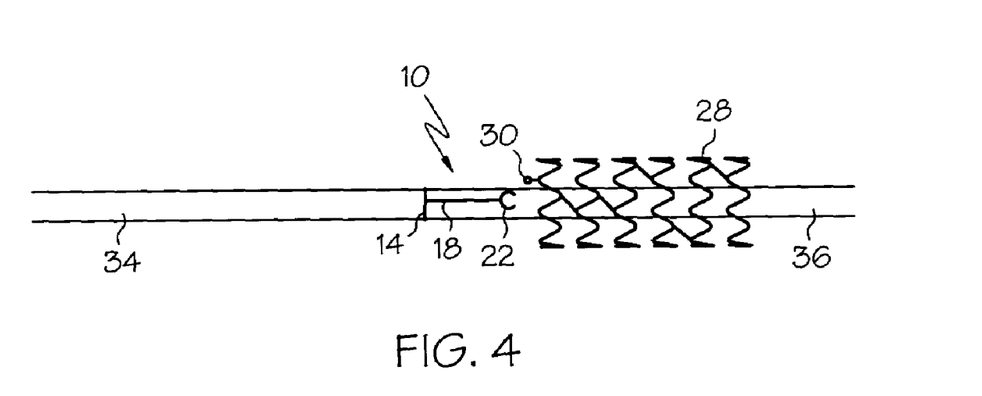
FIG. 4 is a perspective view of an embodiment of an inventive stent securement member placed on a catheter after deflation of the balloon.

Referring to FIGS. 3 and 4, upon expansion of the balloon 36, the stent 28 is expanded. The flexible connecting member 18 is desirably sufficiently flexible and of sufficient length to allow displacement of the locking member 22 in a stent radial direction equal to the radial expansion of the stent 28. During expansion, the securement member 10 prevents movement of the stent engagable portion 30 in the axial direction, thereby preventing stent lengthening or foreshortening. Desirably, the securement member 10 will also constrain the stent engagable portion 30 from rotation about the balloon 36.

When the stent 28 has reached the full deployment diameter, the balloon 36 is deflated. Upon deflation, the securement member 10 desirably returns to its original reduced configuration. Desirably, this is accomplished by pseudo-elastic effect of the flexible connecting member 18. Desirably, the temperature at which the Austenite phase of the shape memory alloy finishes forming is lower than human body temperature. Thus, throughout the entire time period that the securement member 10 remains in the body, the shape memory alloy will remain in the pseudo-elastic state.

Alternatively, the shape memory alloy may be deformed in the Martensitic state. The flexible connecting member 18 may be returned to its original reduced configuration by introducing a heated fluid into the vessel. The shape memory alloy desirably experiences a phase change and transforms to an Austenitic state upon introduction of the heated fluid.

During deflation of the balloon 36, the securement member 10 may additionally apply pressure to the balloon 36, resulting in faster deflation times. As the balloon 36 deflates, the securement member locking member 22 becomes disengaged from the stent engagable portion 30.

Upon proper deflation of the balloon 36, the catheter 34, deflated balloon 36 and securement member 10 are free to move independently from the stent 28. Thus, the catheter 34, balloon 36 and securement member 10 may be removed from the patient.

In another embodiment, the present invention is directed to a stent securement member 10 as depicted in FIGS. 5-8. The securement member 10 generally comprises a securement connector 14, a plurality of flexible connecting members 18 and a plurality of locking or engaging members 22. The flexible connecting members 18 may form a serpentine circumferential band.

The securement member 10 may be used with a stent 28 having a plurality of engagable portions 30 desirably located at one or both ends of the stent 28. The locking members 22 are arranged to engage the stent engagable portions 30 and thereby constrain movement of the stent 28. Desirably, movement of the stent 28 at the stent engagable portions 30 will be constrained in two dimensions. The securement member 10 will prevent movement in the stent axial direction, as well as preventing rotation of the stent 28 about the balloon. Desirably, the securement member 10 will not restrain movement in the direction of radial expansion of the stent 28.

Figure 5:
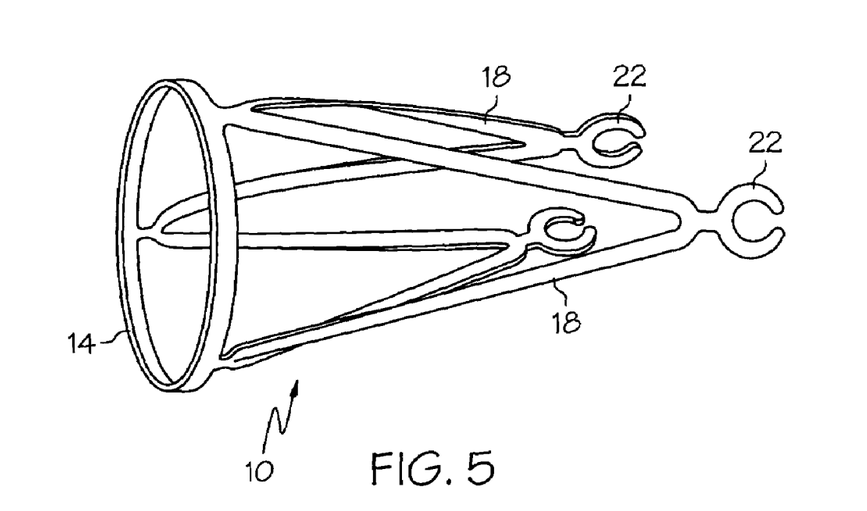
FIG. 5 is a perspective view of an embodiment of an inventive stent securement member.
Figure 6:
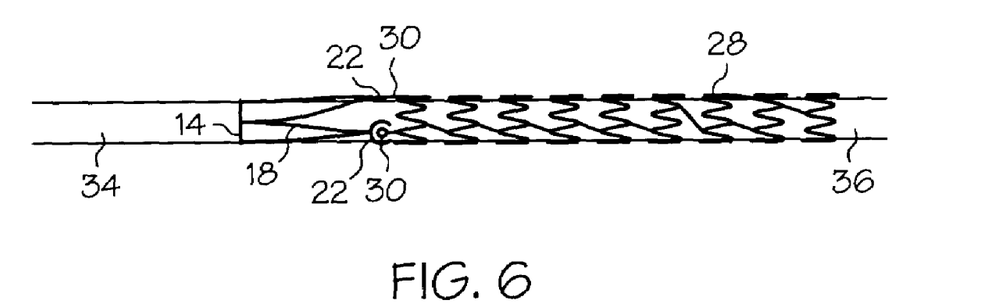
FIG. 6 is a perspective view of an embodiment of an inventive stent securement member placed on a catheter with a stent in the reduced state.

The securement member 10 will typically be used during stent delivery in conjunction with a catheter 34 and an expansion balloon 36. A balloon expandable stent 28 is typically crimped in a reduced state around a balloon 36 and catheter 34. The securement member 10 may be placed upon the catheter 34 with the locking members 22 engaging the stent engagable portions 30 appropriately. The securement connector 14 may be coupled to the catheter 34 shaft, desirably by swaging or by having a diameter of appropriate size to frictionally engage the catheter 34. Although the securement connector 14 desirably encircles the catheter 34, the securement connector 14 may be of any size, shape or material that adequately engages the catheter 34. The flexible connecting members 18 desirably overlay a portion of the expandable balloon 36 when the securement member 10 is in place.

The flexible connecting members 18 are desirably made from a shape memory material, such as NiTi, CuZnAl, CuAlNi, MP35N, Elgiloy, Phynox, TiPtNi, TiPdNi, Cu—Zn, Cu—Al, Fe—Cr—Ni, Fe—Pd or Fe—Pt. The shape memory material may also be a polymer such as polymethylmethacrylate, polyvinylchloride, polynorbornene, trans-polyisoprene, polyurethane, styrene-butadiene copolymer or polyethylene. Further, the flexible connecting members 18 desirably will normally return to this reduced configuration.

Figure 7:
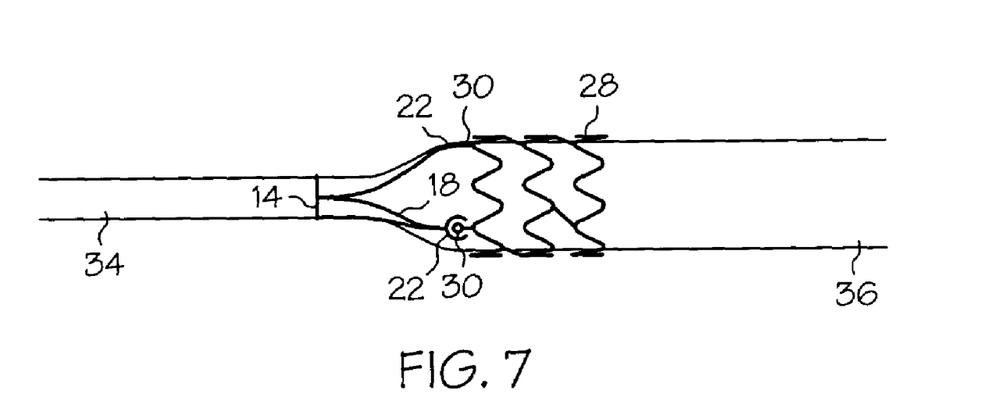
FIG. 7 is a perspective view of an embodiment of an inventive stent securement member placed on a catheter with a stent, wherein the expansion balloon is expanded.
Figure 8:
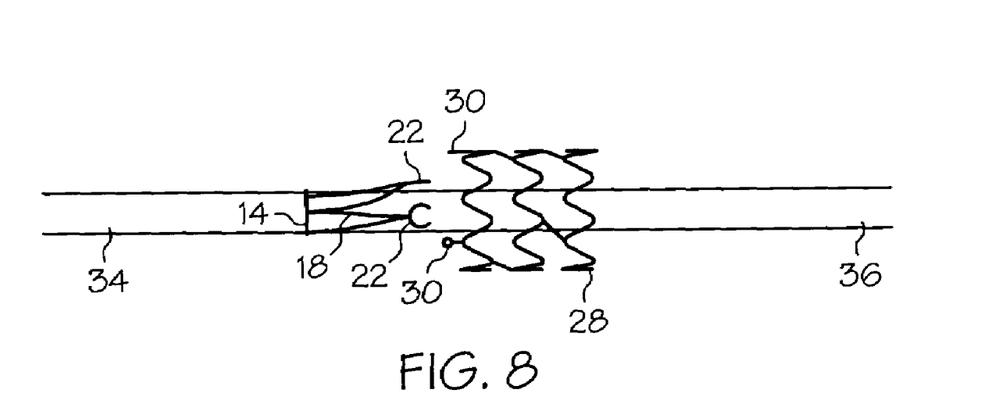
FIG. 8 is a perspective view of an embodiment of an inventive stent securement member placed on a catheter after deflation of the balloon.

Referring to FIGS. 7 and 8, upon expansion of the balloon 36, the stent 28 becomes expanded. The flexible connecting members 18 are desirably sufficiently flexible and of sufficient length to allow displacement of the locking members 22 in a stent radial direction equal to the radial expansion of the stent 28. During expansion, the securement member 10 prevents movement of the stent engagable portion 30 in the axial direction, thereby preventing stent lengthening or foreshortening. Desirably, the securement member 10 will also constrain the stent engagable portion 30 from rotation about the balloon 36. Further, multiple locking members 22 help to accomplish a uniform and proportional circumferential expansion of the stent 28.

When the stent 28 has reached the full deployment diameter, the balloon 36 is deflated. Upon deflation, the securement member 10 desirably returns to its original reduced configuration. Desirably, this is accomplished by pseudo-elastic effect of the flexible connecting members 18. Desirably, the temperature at which the Austenite phase of the shape memory alloy finishes forming is lower than human body temperature. Thus, throughout the entire time period that the securement member 10 remains in the body, the shape memory alloy will remain in the pseudo-elastic state.

Alternatively, the shape memory alloy may be deformed in the Martensitic state. The flexible connecting member 18 may be returned to its original reduced configuration by introducing a heated fluid into the vessel. The shape memory alloy desirably experiences a phase change and transforms to an Austenitic state upon introduction of the heated fluid.

During deflation of the balloon 36, the securement member 10 may additionally apply pressure to the balloon 36, resulting in faster deflation times. As the balloon 36 deflates, the securement member locking members 22 become disengaged from the stent engagable portions 30.

Upon proper deflation of the balloon 36, the catheter 34, deflated balloon 36 and securement member 10 are free to move independently from the stent 28. Thus, the catheter 34, balloon 36 and securement member 10 may be removed from the patient.

Further embodiments of the invention are depicted in FIGS. 9-15.

Figure 9:
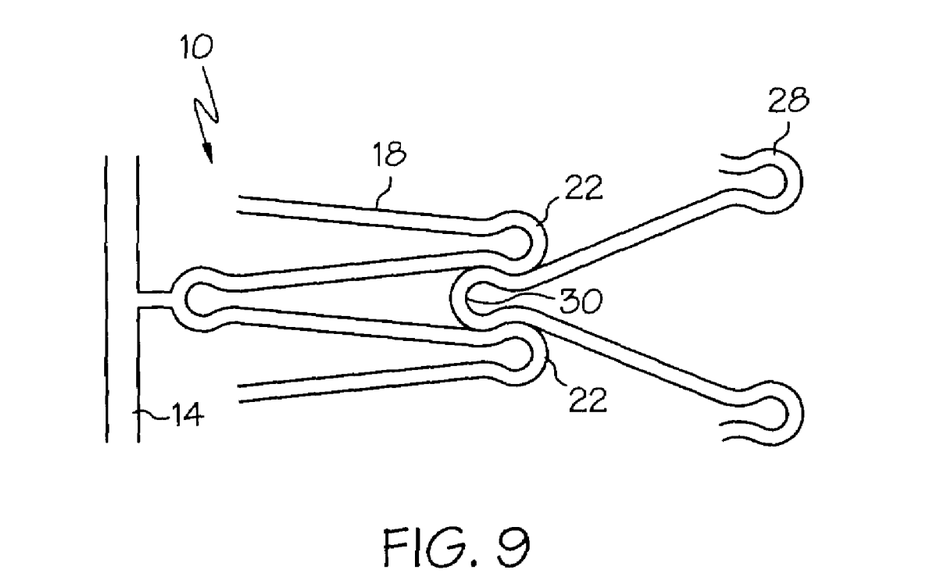
FIG. 9 shows another embodiment of an inventive stent securement member.

FIG. 9 shows an embodiment of a securement member 10 comprising a securement connector 14, a plurality of flexible connecting members 18 and a plurality of locking or engaging members 22. The flexible connecting members 18 form a serpentine circumferential band, and locking members 22 work in conjunction with each other to engage the stent engagable portion 30. Further, the stent engagable portion 30 in this embodiment may be a rounded peak at an end portion of the stent 28.

Figure 10:
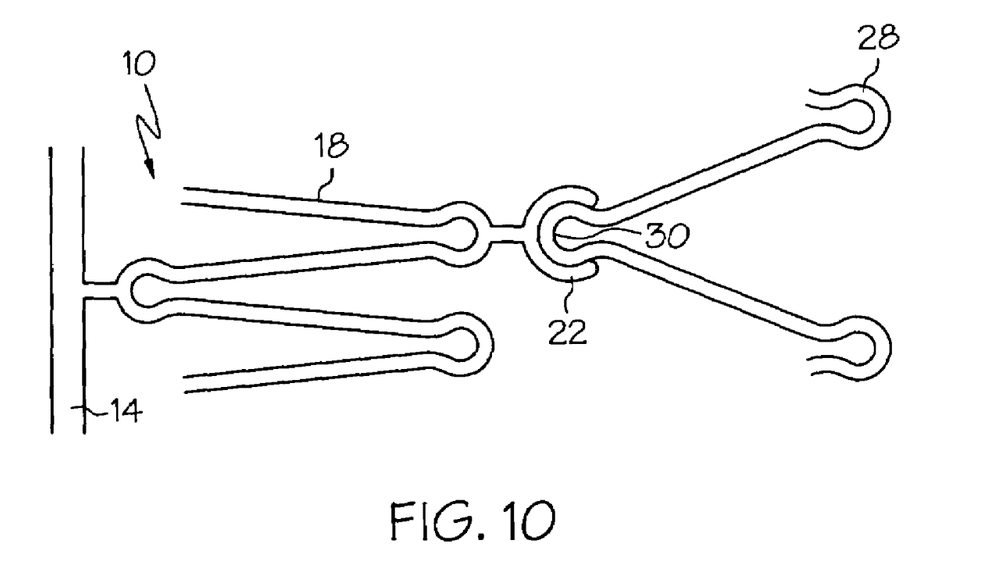
FIG. 10 shows another embodiment of an inventive stent securement member.

FIG. 10 shows an embodiment of a securement member 10 comprising a securement connector 14, a plurality of flexible connecting members 18 and at least one locking or engaging member 22. The flexible connecting members 18 form a serpentine circumferential band, and locking members 22 are formed on a portion of the serpentine circumferential band peaks. The stent engagable portion 30 in this embodiment may be a rounded peak at an end portion of the stent 28.

Figure 11:
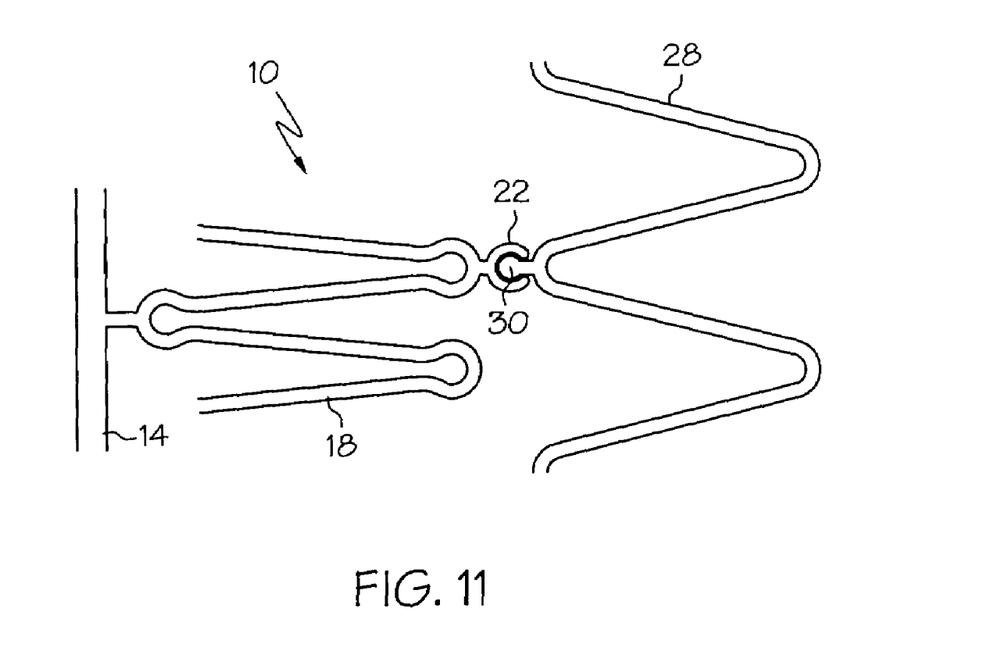
FIG. 11 shows another embodiment of an inventive stent securement member.

FIG. 11 shows an embodiment of a securement member 10 comprising a securement connector 14, a plurality of flexible connecting members 18 and at least one locking or engaging member 22. The flexible connecting members 18 form a serpentine circumferential band, and locking members 22 are formed on a portion of the serpentine circumferential band peaks.

Figure 12:
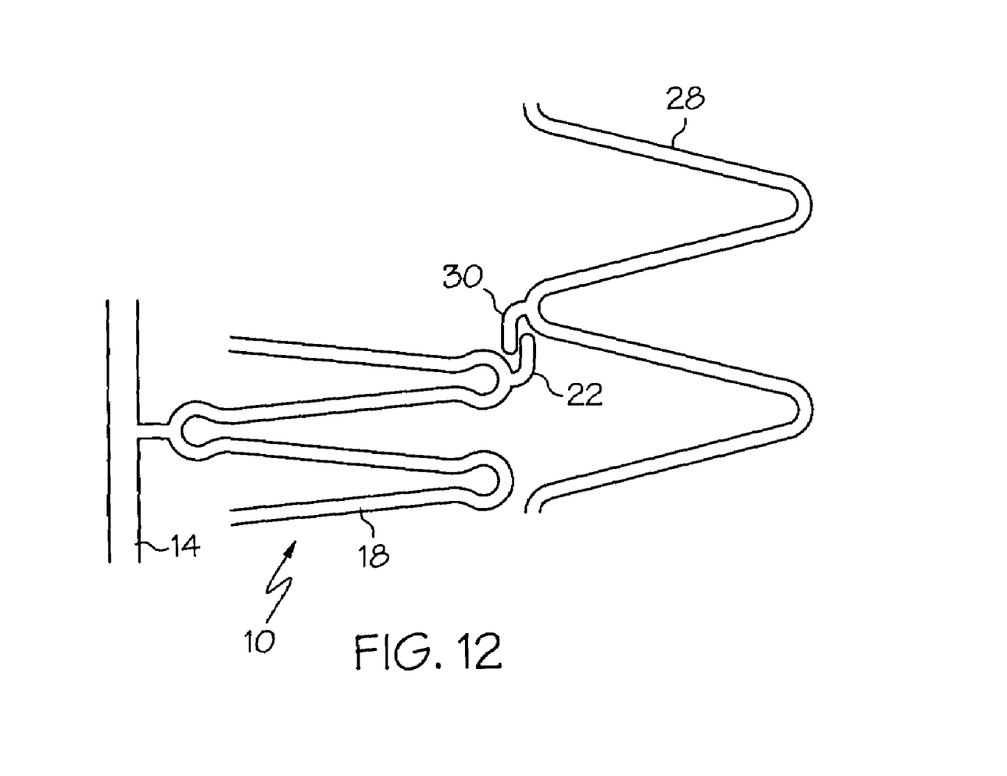
FIG. 12 shows another embodiment of an inventive stent securement member.

FIG. 12 shows an embodiment of a securement member 10 comprising a securement connector 14, a plurality of flexible connecting members 18 and at least one locking or engaging member 22. The flexible connecting members 18 form a serpentine circumferential band, and locking members 22 are formed on a portion of the serpentine circumferential band peaks. The locking members 22 of this embodiment are designed to engage the stent engagable portion 30 to constrict motion in only the axial direction.

Figure 13:
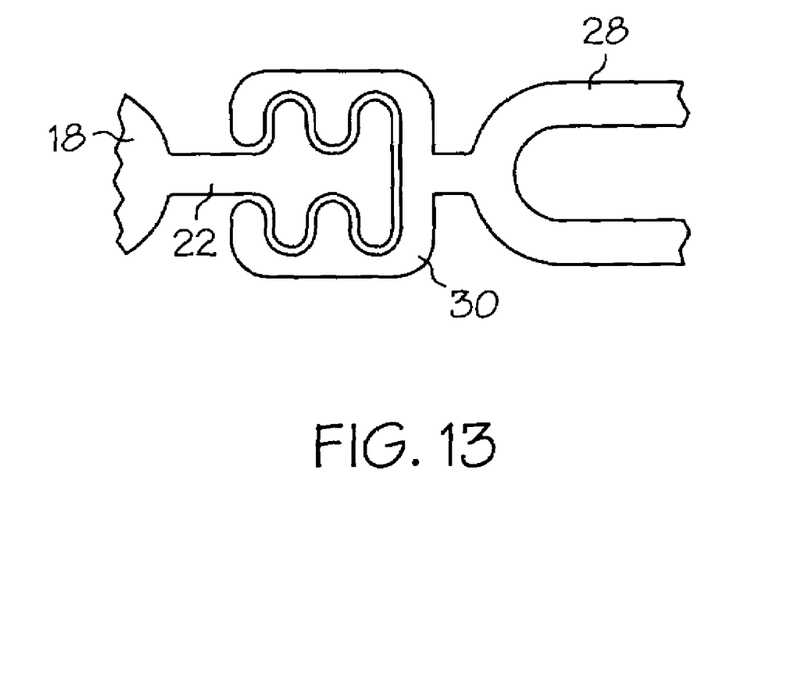
FIG. 13 shows another embodiment of an inventive stent securement member.

FIG. 13 shows another embodiment of a securement member 10. Locking members 22 in this embodiment comprise an "I" or an "H" shape, and stent engagable portions 30 are suitably shaped to receive the locking members 22.

Figure 14:
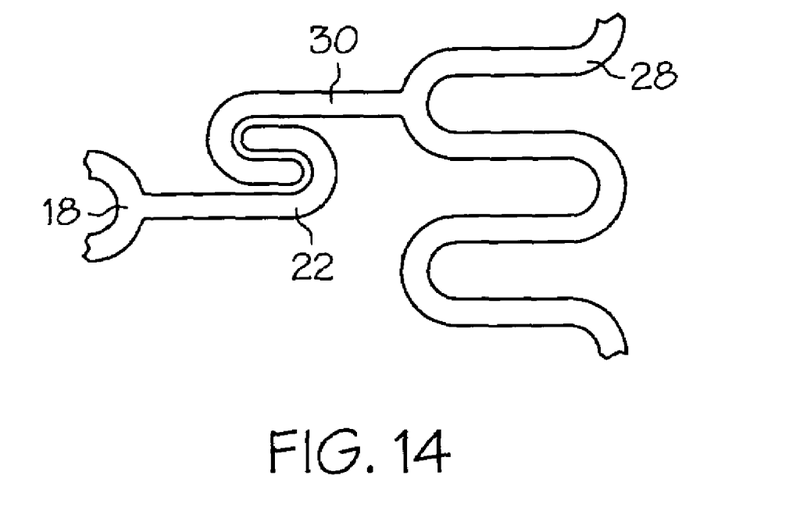
FIG. 14 shows another embodiment of an inventive stent securement member.

FIG. 14 shows another embodiment of a securement member 10. Locking members 22 and stent engagable portions 30 comprise hooks in this embodiment.

Figure 15:
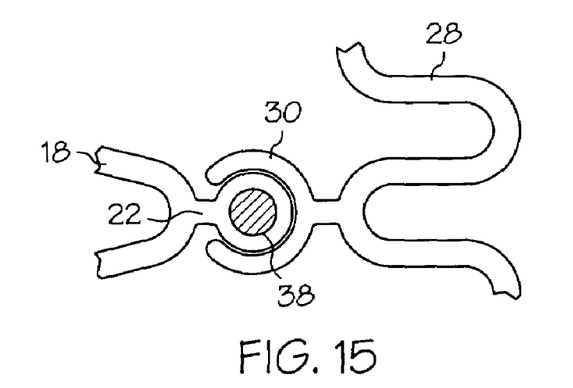
FIG. 15 shows another embodiment of an inventive stent securement member having a radiopaque marker.

FIG. 15 shows another embodiment of a securement member 10. Locking members 22 in this embodiment further may include a radiopaque marker 38.

Figure 16:
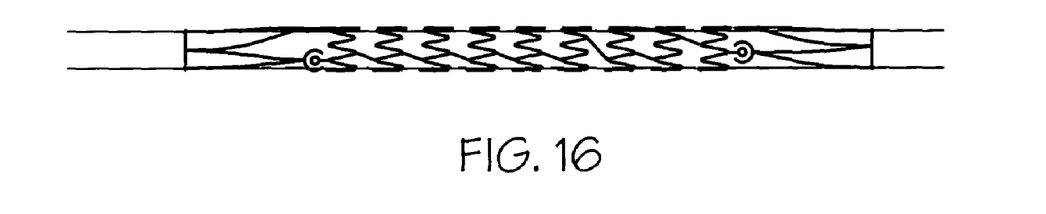
FIG. 16 is a perspective view of an embodiment of inventive stent securement members placed on a catheter with a stent in the reduced state.

Although only one securement member 10 has been shown attached to a catheter in FIGS. 1-8, it is within the purview of the invention to use multiple securement members 10 in conjunction with a single stent 28. Desirably, one securement member 10 will be used at each end of the stent 28, as depicted in FIG. 16. Optionally a plurality of securement members may be used at one or both ends of the stent. Thus, for example, one end of the stent may be provided with two or more securement members.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the various embodiments of the invention. Those skilled in the art may recognize other equivalents to the specific embodiment described herein which equivalents are intended to be encompassed by the claims attached hereto.

The invention claimed is:

1. A device for preventing stent movement during delivery comprising:
    a securement connector arranged to engage an outer surface of a catheter;
    at least one flexible connecting member made from a shape memory material, said flexible connecting member comprising a serpentine band, said shape memory material having an Af temperature lower than normal human body temperature, said at least one flexible connecting member being balloon expandable, said flexible connecting member having a first end portion and a second end portion, the first end portion coupled to said securement connector; and
    a locking member located at said flexible connecting member second end portion arranged to engage a portion of a stent;
    wherein a diameter of the securement connector remains constant during stent expansion.

2. The device of claim 1, further comprising a plurality of flexible connecting members.

3. The device of claim 2, wherein said flexible connecting members are arranged to expand with the stent.

4. In combination, the device of claim 1 and a catheter, the catheter having a balloon with a stent disposed thereabout, the stent engaged to the device.

5. The combination of claim 4 wherein the stein includes an engagable portion arranged to engage said looking member.

6. The combination of claim 5 wherein the device is made of a shape memory material which is balloon expandable and which is programmed to return an unexpanded diameter following balloon expansion.

7. The device of claim 1, wherein the shape memory material comprises a shape polymer.

8. The device of claim 1, wherein the securement connector is fixedly attached to the catheter.

9. The device of claim 1, where the flexible connecting member comprises a length between the first end portion and the second end portion, and a point on the stent experiences radial displacement upon stent expansion, the length being greater than the radial displacement.

10. A device for preventing stent movement during delivery comprising:
    a securement connector arranged to engage an outer surface of a catheter;
    a plurality of flexible comprising members, each of said flexible connecting members made from a shape memory material, each of said flexible connecting members having a first end portion and a second end portion, the first end portion coupled to said securement connector, wherein the flexible connecting members comprise a serpentine band; and
    a locking member located on each of said flexible connecing members second end portion arranged to engage a portion of a stent in a way that allows freedom of movement in a radial direction between the locking member and the stent;
    wherein a diameter of the securement connector remains constant during stent expansion.

11. The device of claim 10, wherein at least one of the flexible connecting members is balloon expandable.

12. The device of claim 10, wherein the shape memory material has an Af temperature lower than normal human body temperature.

13. A stent delivery system comprising:
    a catheter comprising an expandable balloon and a proximal shaft portion, the proximal shaft portion located proximal to said expandable balloon along the length of the catheter;
    a radically expandable stent having at least one engagable portion;
    at least one radically expandable constrainment member having a first end coupled to said catheter proximal shaft portion and a second end having at least one engaging portion;
    wherein the at least one constrainment member is in the form of a serpentine shaped wherein said constrainment: member engaging portion and said stent engagable portion band and;
    wherein said constrainment; member engaging portion and said stent engagable portion are engaged;
    and wherein said constrainment member ingaging portion and said stent engagable portion may remain engaged throughout the expansion of said balloon.

14. The stent delivery system of claim 13, wherein said constrainment member engaging portion and said stent engagable portion are constructed and arranged to disengage when said balloon is deflated.

15. The stent delivery system of claim 14, wherein said constrainment member is made from a shape memory material.

16. A stent delivery system comprising:
a catheter;
an expandable balloon;
a radially expandable stent having at least one engagable portion;
at least one radically expandable constrainment member having a first end coupled to said catheter and a second end having at least one engaging portion;
wherein said constrainment member engaging portion and said stout engagable portion are engaged and are constructed and arranged to remain engaged until said balloon is at least partially deflated; and
wherein the constrainment member is in the form of a serpentine shaped band: and
wherein the constrainment is made from a shape memory material and is programmed to return to a reduced diameter configuration following balloon expansion.

17. A stent delivery system comprising:
a catheter comprising an expandable balloon and a proximal shaft portion, the proximal shaft portion located proximal to said expandable balloon along the length of the catheter;
a radially expandable stent having at least one expandable portion;
at least one radially expandable constrainment member having a first end coupled to said catheter proximal shaft portion and a second end having at least one engaging portion;
wherein said constrainment member ingaging portion and said stent engagable portion are engaged; and
wherein said constrainment member engaging portion and said stent engagable portion are in the form of a ball and socket:
and wherein said constrainment member engaging portion and said stent engagable portion may remain engaged throughout the expansion of said balloon.

18. A stent delivery system comprising:
a catheter comprising an expandable balloon and a proximal shaft portion, the proximal shaft portion located proximal to said expandable balloon along the length of the catheter;
a radially expandable stent arranged about said expandable balloon in an unexpanded state, said stent having an end portion, said end portion having at least one engagable portion;
at least one radially expandable constrainment member arranged to partially overlay said balloon, said constrainment member having a first end coupled to said catheter proximal shaft portion, the constrainment member further comprising a serpentine band having a plurlality of openings therethrough and an engaging portion;
wherein said constrainment member engaging portion is arranged to engage said stent engagable portion;
and wherein when said constrainment member engaging portion and said stent engagable portion are engaged, movement of said stent engagable portion in the axial direction is prevented.

19. The stent delivery system of claim 18, wherein when said constrainment member engaging portion and said stent engagable portion are engaged, said stent engagable portion is further constrained from rotation about the catheter.

20. The stent delivery system of claim 18, wherein when said constrainment member engaging portion and said stent engagable portion are engaged, said stent engagable portion is free to move in the direction of radial expansion.

21. A device for preventing stent movement during delivery comprising:
a securement connector arranged to engage an outer surface of a catheter;
at least one flexible connecting member made from a shape memory material, said flexible connecting member comprising a serpentine band, said flexible connecting member having a first end portion and a second end portion, the first end portion coupled to said securement connector; and
a locking member located at said flexible connecting member second end portion arranged to engage a portion of a stent;
wherein a diameter of the securement connector remains constant during stent expansion; and wherein the shape memory material comprises a shape memory alloy having an Austenite phase and a Martensite phase.

* * * * *